US005891153A

United States Patent [19]
Peterson

[11] Patent Number: 5,891,153
[45] Date of Patent: Apr. 6, 1999

[54] AUGER NUCLEUS EXTRACTED FOR CATARACTS

[76] Inventor: Randy Peterson, 3129 Lochridge La., Springfield, Ill. 62704

[21] Appl. No.: 997,127

[22] Filed: Dec. 23, 1997

[51] Int. Cl.⁶ ........................................... A61F 9/00
[52] U.S. Cl. ........................... 606/107; 606/113; 606/167
[58] Field of Search ..................... 606/107, 106, 606/170, 159, 167, 1, 110, 113, 127, 128, 184, 185

[56] References Cited

U.S. PATENT DOCUMENTS

| | | | |
|---|---|---|---|
| 3,320,957 | 5/1967 | Sokolik | 606/170 |
| 3,732,858 | 5/1973 | Banko . | |
| 3,739,784 | 6/1973 | Itoh . | |
| 3,791,387 | 2/1974 | Itoh . | |
| 3,906,954 | 9/1975 | Baehr et al. . | |
| 3,908,661 | 9/1975 | Kramer . | |
| 3,945,375 | 3/1976 | Banko . | |
| 3,976,077 | 8/1976 | Kerfoot, Jr. . | |
| 4,061,146 | 12/1977 | Baehr et al. . | |
| 4,111,208 | 9/1978 | Leuenberger . | |
| 4,611,594 | 9/1986 | Grayhack et al. . | |
| 4,773,415 | 9/1988 | Tan . | |
| 5,098,441 | 3/1992 | Wechler | 606/113 |
| 5,171,314 | 12/1992 | Dulebohn | 606/113 |
| 5,176,688 | 1/1993 | Narayan et al. | 606/128 |
| 5,190,561 | 3/1993 | Graber | 606/127 |
| 5,197,968 | 3/1993 | Clement | 606/115 |
| 5,312,417 | 5/1994 | Wilk | 606/114 |
| 5,330,482 | 7/1994 | Gibbs et al. | 606/113 |
| 5,431,671 | 7/1995 | Nallakrishnan | 606/167 |
| 5,496,330 | 3/1996 | Bates et al. | 606/127 |
| 5,709,697 | 1/1998 | Ratcliff et al. | 606/180 |

*Primary Examiner*—Glenn K. Dawson
*Assistant Examiner*—Vy Q. Bui
*Attorney, Agent, or Firm*—Marshall, O'Toole, Gerstein, Murray & Borun

[57] ABSTRACT

A surgical instrument for removing the cataractous nucleus from the eye. The instrument consists of a proximal handle and plunger. The plunger also acts as a screw-drive for an auger located at the distal end of the instrument. The screw-drive plunger is advanced exposing a nucleus encasing basket at the distal end of the instrument. The nucleus is completely encased in the distal basket and slowly ground up by the auger, removing the nucleus from the eye in its entirety. The use of unique internal gearing between the auger and encasing element results in a safe, efficient, controllable evacuation of the nucleus from the eye.

16 Claims, 5 Drawing Sheets

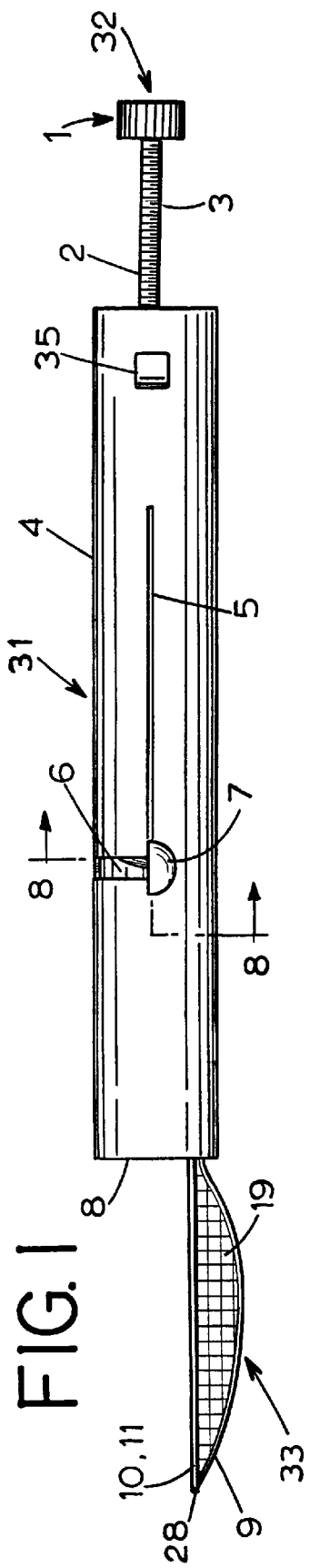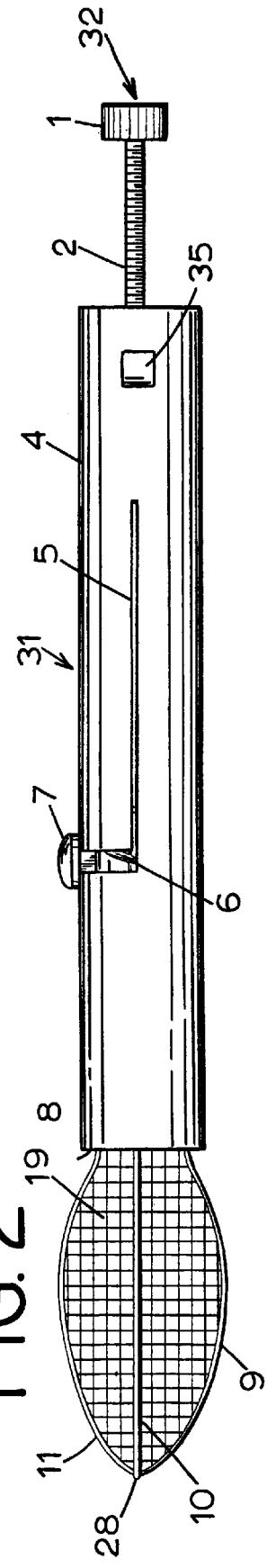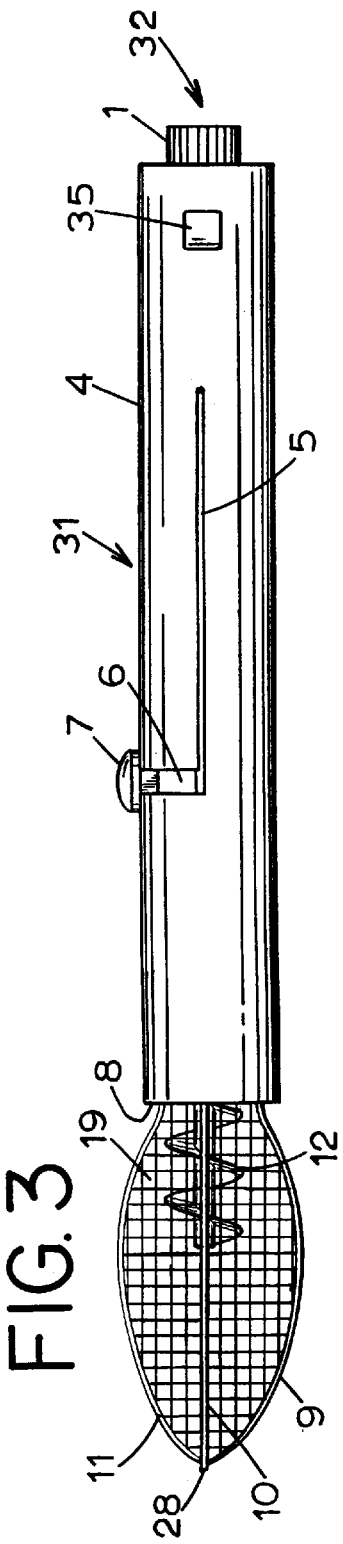

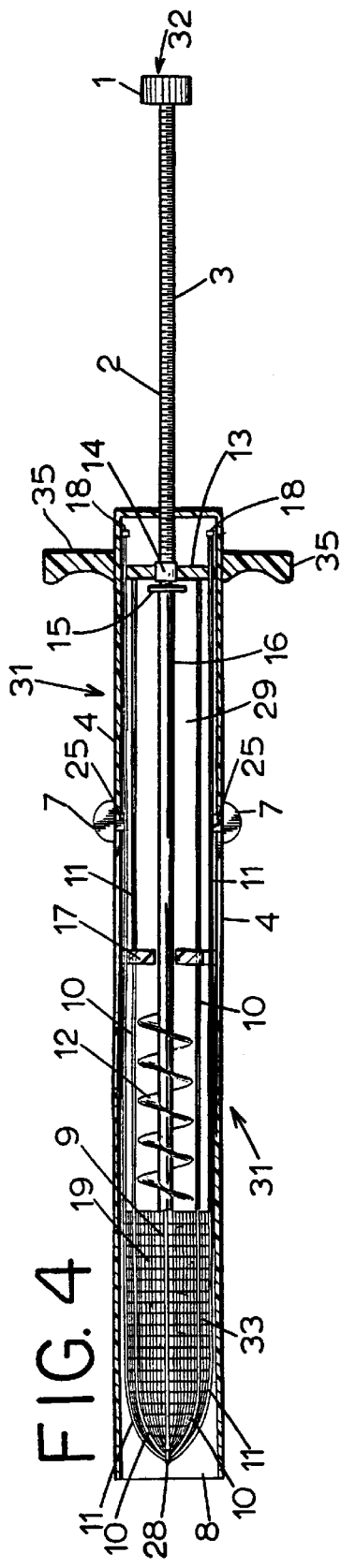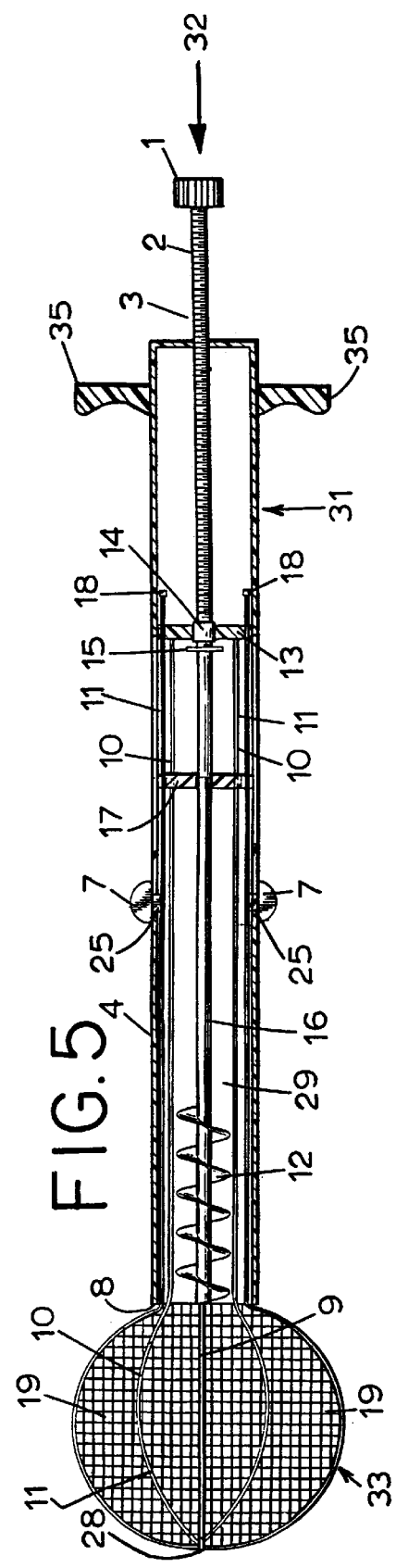

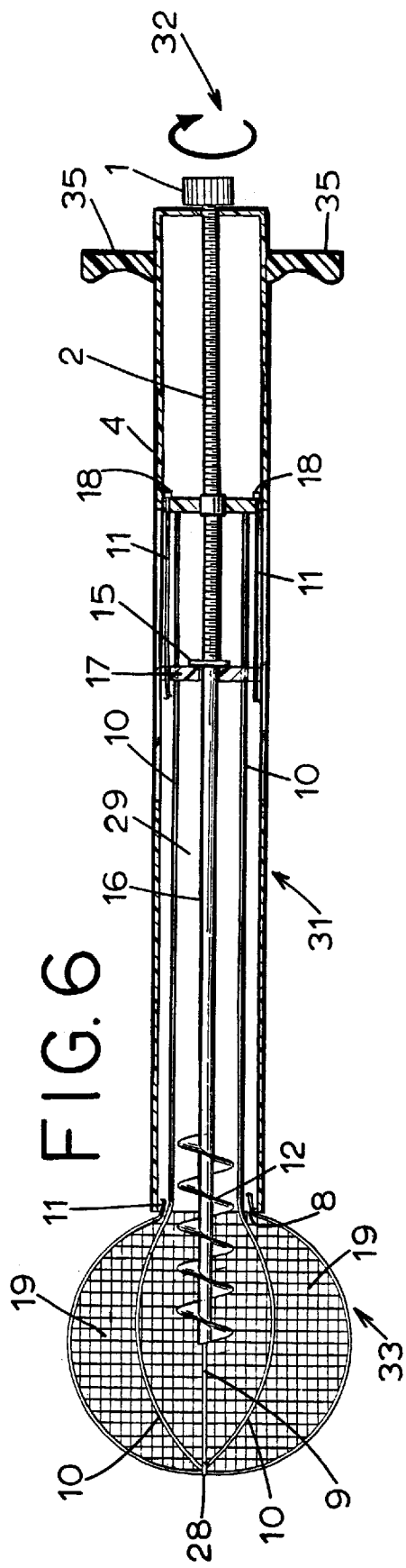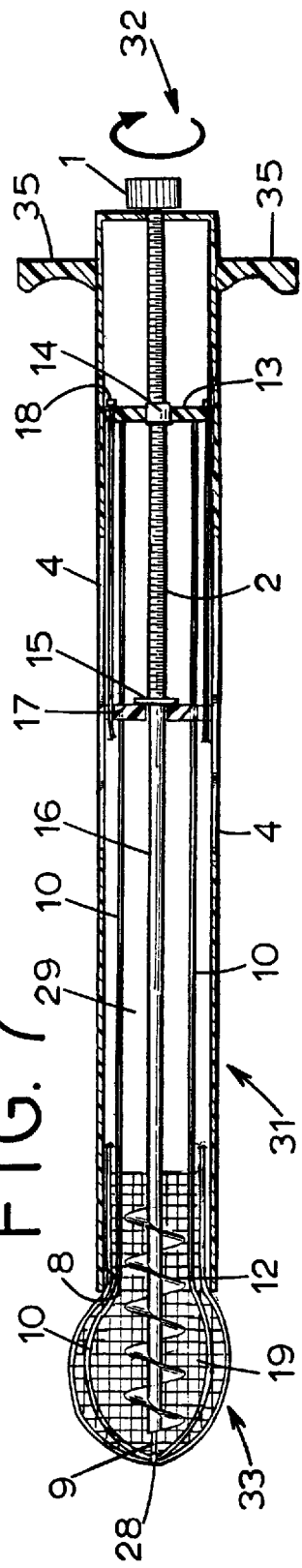

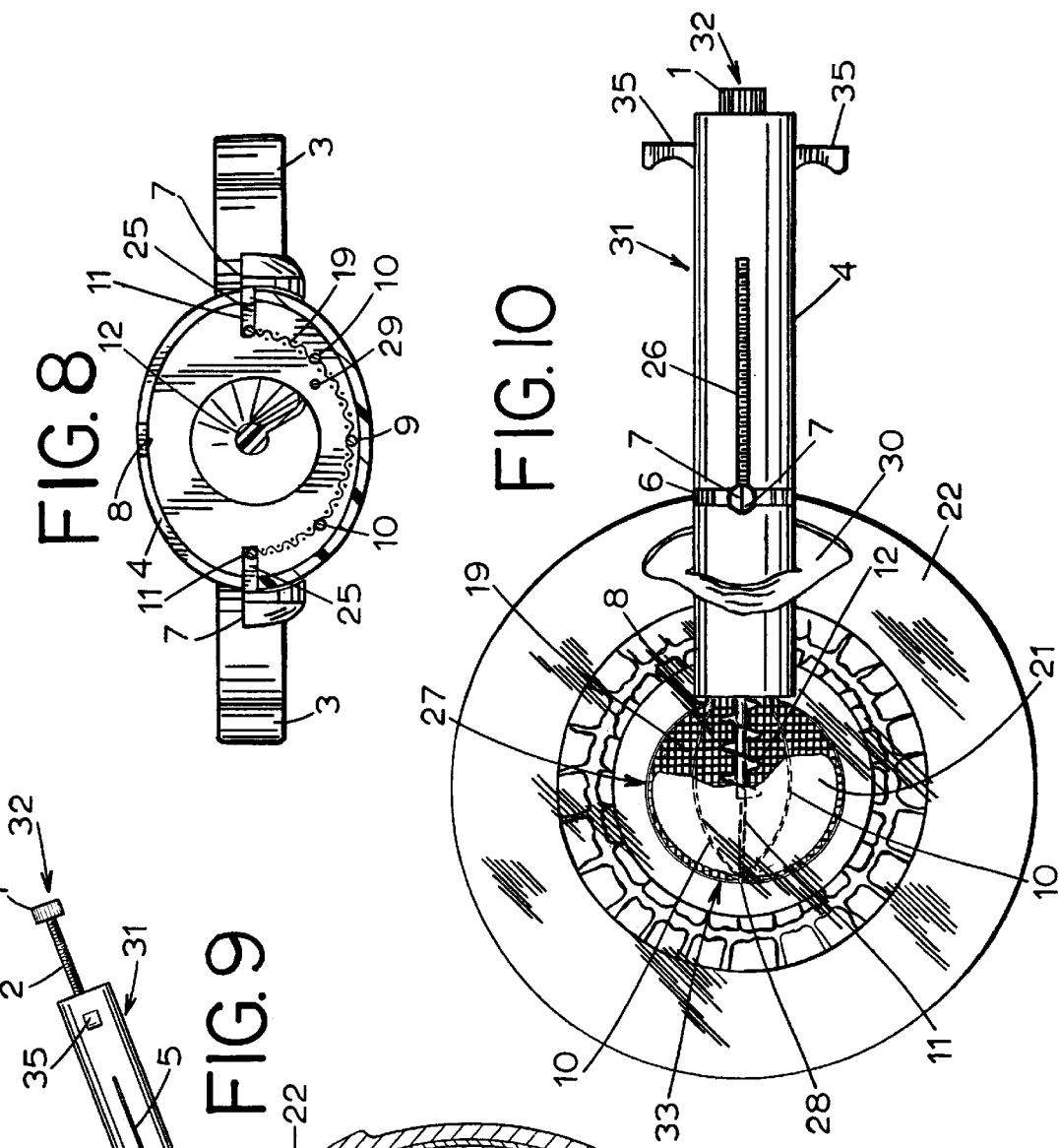
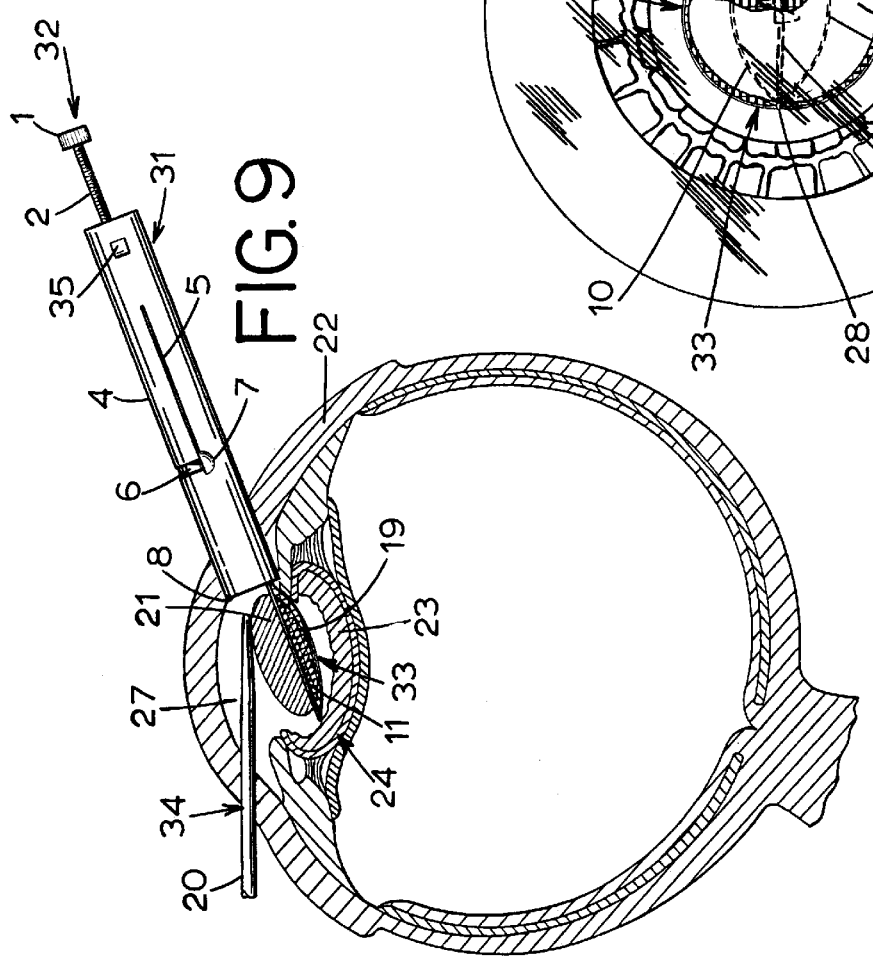

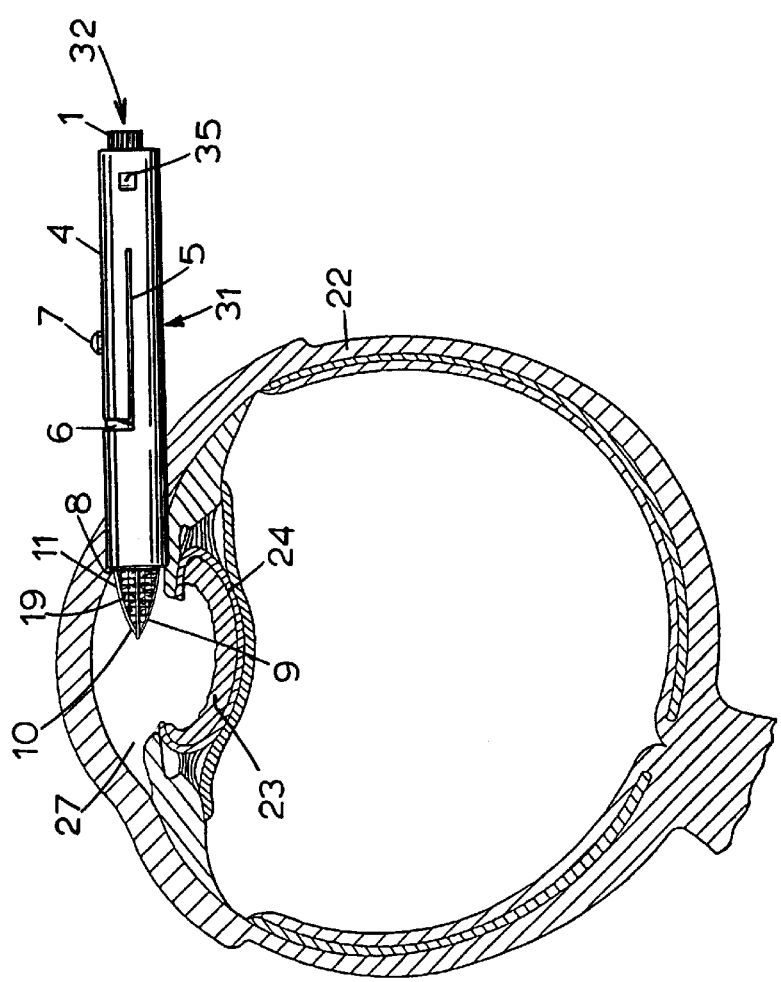
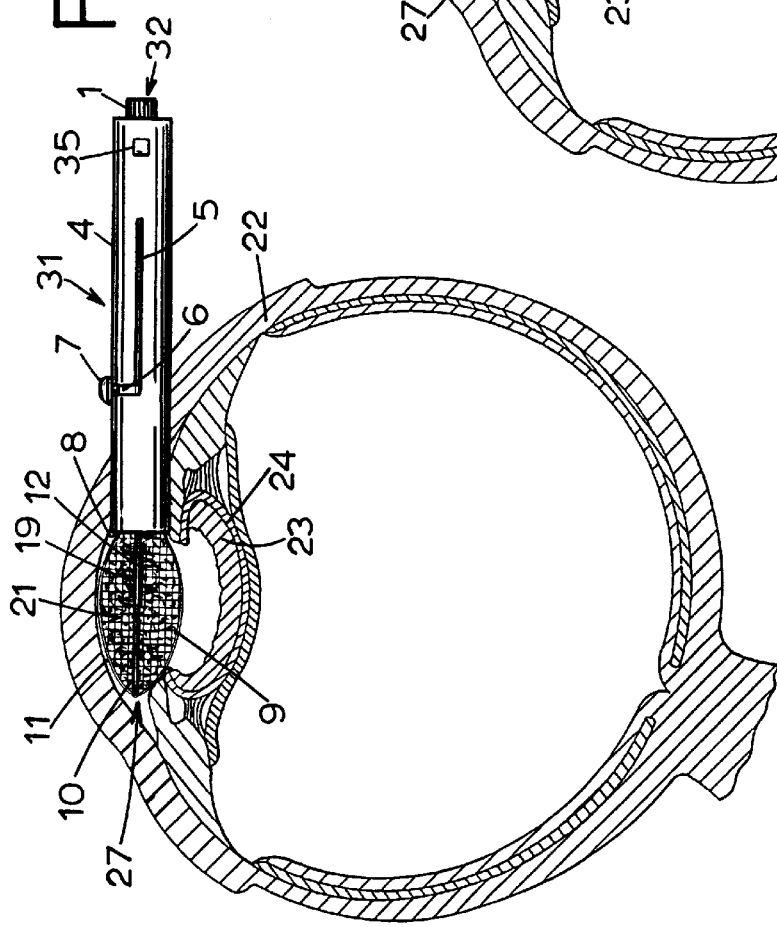

AUGER NUCLEUS EXTRACTED FOR CATARACTS

BACKGROUND OF THE INVENTION

The invention relates to medical instruments, and more specifically, to surgical instruments for removing cataracts from the eye.

A cataract is defined as any opacity in the lens or as any lenticular opacity that interferes with vision. Once visual function has been compromised by cataract the only effective means of treatment is surgery to remove the lens. Cataract is the most prevalent, visually disabling eye disease in the world. It is estimated that 30 to 45 million people in the world are blind, with cataract accounting for as much as 45% of this blindness. Cataracts were treated in the second half of the 18th century in Europe by couching or reclination. Couching was performed by piercing the sclera with a sharp lancet and then inserting a blunt instrument used to depress the lens into the vitreous. Incisional techniques for cataract extraction were first reported in the mid 18th century. Such techniques involved making a large incision in the cornea and removing the entire lens from the eye with the capsule intact (intracapsular). Many methods of intracapsular cataract extraction were subsequently developed. All of these methods require large 180 degree (12 mm) incisions which were unstable and required prolonged recovery. The quest for small incisional cataract wounds, a safe scaffolding to hold intraocular lenses and decreased postoperative complications all led to the decline in intracapsular cataract surgery in the 1970's.

Several techniques are presently employed in surgical practice for removal of cataracts from the eye. Regardless of the technique, cataract surgery requires making a small incision in the eye, and removing the cataract from the eye through this incision. Experience has shown the incision size in cataract surgery to be important. Smaller incisions result in more rapid post operative recovery and a more structurally stable eye. Today, the preferred surgical method of cataract extraction is extracapsular, either by standard extracapsular extraction or by phacoemulsification.

Standard extracapsular cataract surgery involves making an incision (4–7 mm) and either removing the cataractous nucleus intact or fragmenting the nucleus and mechanically removing the pieces through the incision. In general the smaller the incision the more fragmentation of the cataract is required to remove it from the eye. Regardless of the instruments used, the production of multiple fragments is technically more difficult and more likely to cause intraoperative complications than simple removal of a cataract though a larger incision.

In an effort to overcome the problems inherent in removing a cataract though a small incision (3–5 mm) in a safe, technically simple and cost effective way, a number of medical instruments have been developed. Some of these instruments incorporate a screw-like rotating cutting tool to break up the cataract. Banko U.S. Pat. No. 3,732,858 discloses an apparatus for removing blood clots, cataracts and other objects from the eye. This apparatus consist of a central rotating cutting element surrounded by a housing with an open end. By controlling the relative movement of the outer and inner aspects of the cutting instrument, objects engaged in the cutting end of the instrument are ground up and removed from the eye. Engaging the material to be removed from the eye is aided by differential pressure developed by a pressure control apparatus.

Banko U.S. Pat. No. 3,945,375 discloses a surgical instrument for removing tissue including a rotating fluted cutter member housed in a probe adapted for insertion into a body cavity. The instrument can supply irrigation fluid and evacuate the material after being engaged by the cutter. The cutting tool includes a shaft, a fluted drill type cutter, and a shank whose end is fastened to a holder. The holder has a partial internal bore which fits over a motor shaft.

Baehr et al., U.S. Pat. No. 3,906,954 disclose a surgical tissue macerating and removal tool with a high speed rotating cutting tip powered by an air turbine. A fluid pump is provided to evacuate macerated material and treatment fluid from the eye. Means are also provided for axially positioning the rotating cutting member.

Kerfoot, Jr. U.S. Pat. No. 3,976,077 discloses a surgical device with a rotary shaft having helical threads terminating in a cutting tip. The shaft is rotated at high speed and fluid is supplied to the cutting tip to aid in the maceration of the material being removed by the machine. The macerated material and the working fluid are withdrawn from the operative site by the pumping action of the rotating helical threads of the shaft.

Baehr et al., U.S. Pat. No. 4,061,146 disclose a surgical tissue macerating and removal tool having a rotating rod with a cutting member that resembles a screw. The tissue engaging end of the instrument also includes a tapering frusto-conical member which surrounds the rotating cutting tool. The frusto-conical member restricts rotation of captured tissue undergoing maceration.

These and other surgical instruments utilizing "screw-like" distal cutting elements have certain common characteristics. Each instrument consists of a small bore rotating cutting element whose cutting action depends on continuous physical contact between the tissue (cataract) and the cutting element. Without a secure method of capturing and holding the tissue (cataract), maintenance of continued contact between the cutting element and tissue (cataract) becomes very difficult. As a result, the unstabilized cataract can move about in the eye causing damage and lessening the efficiency of cutting. Fragments of the cataract are also free to float about inside the eye complicating their removal and increasing the likelihood of damage. Another common characteristic of these instruments is the use of a pressure differential or vacuum to aid in the removal of macerated tissue and aid in stabilizing the cataract. This arrangement can result in significant fluid flow through the eye with concomitant turbulence inside the eye with potential for intraocular damage.

Baehr et al. U.S. Pat. No. 4,061,146 addresses the problem of stabilization of the cataract by adding a frusto-conical housing surrounding the cutting element. This results in improved stabilization of the cataract against the cutting element but still allows for fragments of cataract to be thrown around inside the eye by fluid turbulence. Kramer U.S. Pat. No. 3,908,661 discloses a surgical instrument including an open-topped net or bag (much like a fishnet) mounted on a flexible frame for containing and controlling the cataract within the eye. The net is inserted into the eye and the nucleus placed within the bag. The nucleus is then removed from the eye by withdrawing the net, with enclosed nucleus, from the eye. The insertion and withdrawal of the net is facilitated by a frusto-conical sleeve that inserts into the surgical incision. By withdrawing the basket with contained cataract through the end of the sleeve, the cataract is squeezed causing a major portion of the nucleus to fall into the anterior chamber of the eye and 25% to 30% of the nuclear material being removed from the eye. The fragmented nuclear material remaining in the eye is then removed by well know irrigation aspiration procedures. Although adequate initial containment and control of the nucleus is afforded by the Kramer patent, crushing very hard nuclei requires extreme force with little control or margin for error and leaves a significant percentage of the nucleus still in the eye after withdrawal of the instrument. For such reasons, a more controlled method of capturing and fragmenting the lens must be sought.

Many surgical instruments have been developed for very controlled capture and manipulation of tissues within body cavities. Some of these instruments incorporate wires that extend from distal ends to grab or contain objects. Itoh U.S. Pat. Nos. 3,739,784 and 3,791,387 disclose surgical instruments with distal single and multiple wire loops for capturing and cutting tissues within a body cavity. The multiple loop device has a wire with a pivotally attached loop allowing for longitudinal shifting of the wire in a tube. This permits the second wire to be bulged out from the loop to receive the tissue to be captured.

Dulebohn U.S. Pat. No. 5,176,688 discloses a surgical instrument with a single wire snare at its distal end. The distal end of the instrument is modified so that the cutting edges are not exposed to surrounding tissues, thereby protecting surrounding tissues from being damaged during insertion and while cutting with the instrument.

Grayhack et al. U.S. Pat. No. 5,098,441 disclose an instrument for containment and removal of calculi. The surgical instrument consists of an extendible central grasping device of a conventional "stone basket" type of expandable multiple wire loop system. The grasping device is surrounded by a smooth expandable outer tube. The grasping device captures the stone which is retracted within the smooth outer tube forming a protective closure to prevent injury when the stone is extracted.

Wechler U.S. Pat. No. 5,098,441 discloses a lithotriptor with a plurality of outwardly curved catch wires. The wires are constructed in a stranded fashion to achieve large load transfers while handling calculi.

Narayan et al., U.S. Pat. No. 5,176,688 discloses a surgical instrument for removing calculi from the body with a catch basket consisting of a plurality of wires that surround a reciprocating shaft. The reciprocating shaft extends into the cavity of the wire basket breaking up the captured stone.

Clement U.S. Pat. No. 5,197,968 discloses a surgical apparatus consisting of an expandable wire catch basket with an anvil at the distal end of the basket. A reciprocating cutting member is positioned so that when it is extended, it passes through the basket cavity and impacts the distal anvil, thereby cutting the contained tissue. Suction then removes the cut tissue from the body.

Gibbs et al., U.S. Pat. No. 5,330,482 disclose a surgical device consisting of a composite wire construction extraction device. The composite construction of the wire is intended to extend the operating life of the wire catch basket.

Bates et al., U.S. Pat. No. 5,496,330 discloses a surgical device for removing calculi. The device consists of a plurality of wires with pairs of wires formed along the turn of a helix. This construction allows for a greater number of contact points with the entrapped tissue.

These and other surgical extractors have certain common characteristics. Each retrieval basket comprises a plurality of wires which expand in a symmetrical fashion creating a retrieval basket. The expansion and contraction of the wire catch basket is controlled by means of a mechanism on the proximal end of the instrument.

Phacoemulsification is a more recent surgical method than standard extracapsular cataract surgery and utilizes ultrasonic energy to emulsify a cataract nucleus and aspirate the cataract from the eye through a smaller incision (2.5–3.2 mm) than extracapsular cataract surgery. The advent of foldable intraocular lenses to complete the surgery has resulted in sutureless surgery with virtually immediate visual and functional recovery. For these reasons phacoemulsification has become the most popular method of cataract surgery today. Nevertheless, phacoemulsification is very expensive and requires sophisticated equipment that demands significant expertise to operate safely, particularly in the setting of a mature hard cataract. Moreover, the equipment used for phacoemulsification is complex and expensive. For these reasons there remains a desire for simpler less expensive methods and devices for performing cataract surgery. Such a desired method would provide a surgical instrument for safe, controlled, uncomplicated, removal of the nucleus from the eye regardless of the maturity or hardness of the nucleus and could be inserted into the eye through a 3 to 5 mm incision and remove the nucleus, in its entirety, from the eye without enlarging the surgical incision.

BRIEF SUMMARY OF THE INVENTION

The present invention provides a surgical instrument for removing a lens nucleus from an eye and method for its use. The surgical instrument includes a tubular member having an opening at its distal end and a shaft at least partially disposed within the tubular member. The shaft includes an auger disposed at its distal end and a threaded portion. The surgical instrument is also provided with a retractable guide slidably disposed within the tubular member and threadably engaging the threaded portion of the shaft. In addition, the surgical instrument includes a catch basket having an open position and a closed position. The catch basket operatively engages the retractable guide such that, when the retractable guide is moved distally, the basket advances through the opening of the tubular member, and, such that rotation of the shaft with respect to the retractable guide rotates the auger and retracts the basket at least partially into the tubular member. According to a method of its use, the instrument is inserted into the eye and the nucleus is directed into the catch basket. The nucleus is enclosed in the catch basket and the catch basket is retracted into the instrument while the nucleus is ground in the augur prior to removing the instrument from the eye.

In a preferred embodiment, the surgical instrument is further provided with means for moving the catch basket from the open position to a closed position. In the preferred embodiment, the moving means comprises a peripheral wire secured to a manually engageable guide and the manually engageable guide cooperates with a groove defined in the tubular member. According to a further preferred aspect of the invention the catch basket is secured to the retractable guide by at least one central wire and the device further includes at least one and preferably two peripheral wires which couple the basket to one or more manually engageable guides Further according to this embodiment, at least one peripheral wire slidable engages the retractable guide wherein movement of the guide moves the basket between closed and open positions.

In some embodiments, a distal portion of at least one central wire and a distal portion of at least one peripheral wire form the basket. In such embodiments, the distal portions of the at least one central wire and the at least one peripheral wire are preferably enmeshed in flexible netting.

According to a preferred aspect of the invention, the surgical instrument is provided with a stop limiting distal movement of the shaft to a predefined travel length. Preferably, the stop comprises a partition secured within the tubular member and a stop ring disposed on the shaft. Preferably, rotation of the shaft only retracts the basket into the tubular member after distal movement of the shaft has been arrested by the stop. It is also preferable that, after the stop prevents further distal movement of the shaft, continued rotation of the shaft causes the retractable guide to move proximally along the shaft to thereby retract the basket into the tubular member.

According to a further preferred aspect of the invention, the instrument is further provided with a handle on the proximal end of the shaft to facilitate rotation thereof and finger handles located on the tubular member to facilitate sliding advancement of the shaft with respect to the tubular member. According to a further preferred embodiment, the tubular member has a circular or oval cross section along the majority of its body but has an oval cross section at its distal end. Moreover, the tubular member preferably has a smaller diameter at its distal end than along the remainder of its body.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numeral refer to like parts, and in which:

FIG. 1 is a side view of a surgical nucleus extractor constructed in accordance with this invention with a threaded shaft at a proximal end and an extended catch basket in an open configuration at a distal end.

FIG. 2 is a side view similar to FIG. 1 except with the extended basket in a closed configuration and the finger guides moved to the top of the instrument.

FIG. 3 is a side view similar to FIG. 2 except with the auger extended within the closed catch basket.

FIG. 4 is a cross sectional view of the extractor depicting the catch basket, auger and threaded shaft in a retracted state.

FIG. 5 is a cross sectional view similar to FIG. 4 except with the catch basket extended in the open configuration as in the side view FIG. 1.

FIG. 6 is a cross sectional view similar to FIG. 5 except with the auger extended into the closed catch basket as in the side view FIG. 3.

FIG. 7 is a cross sectional view similar to FIG. 6 except with the catch basket almost completely retracted and the auger extended.

FIG. 8 is a cross sectional view of the extractor taken along lines 8 from the distal end, depicting the catch basket in the open configuration and the centrally located auger, the finger guides, finger guide connections to basket wires and proximal handle are prominently displayed.

FIG. 9 is a side view similar to FIG. 1 except the distal end of the instrument and catch basket are depicted within the anterior chamber of an eye and a cataract nucleus is on the open catch basket.

FIG. 10 is a view similar to FIG. 9 except the view is from the top of the instrument and the catch basket is in the closed configuration completely enclosing the nucleus. In addition, the cut-away portion of the nucleus reveals the auger in the extended configuration.

FIG. 11 is a view similar to FIG. 10 except this is a side view.

FIG. 12 is a view similar to FIG. 11 except the catch basket is partially retracted, the nucleus has been mostly removed, and the auger remains extended (much as in FIG. 7).

DESCRIPTION OF ILLUSTRATIVE EMBODIMENTS

The present invention provides a surgical instrument for safe, controlled, uncomplicated, removal of the nucleus from the eye regardless of the maturity or hardness of the nucleus. The surgical instrument of the invention is particularly useful as it can be inserted into the eye through a 3 to 5 mm incision and remove the nucleus, in its entirety, from the eye without enlarging the surgical incision. The invention further provides a surgical instrument for nucleus extraction from the eye that requires substantially the same or less physician dexterity than required by prior art extraction and fragmentation devices. Such instruments and methods are expected to be particularly useful for treatment in the third world as well as away from major urban centers.

FIG. 1 depicts a side view of one embodiment of the surgical extractor constructed in accordance with the teachings of the invention comprising a tubular member 4 having an opening at its distal end 8; a shaft 2 at least partially disposed within the tubular member 4, the shaft having a threaded shaft portion 3 and a control knob 1 at the proximal end of the instrument 32. The tubular member 4 includes a pair of finger handles 35 and a pair of horizontal guide grooves 5 at opposite sides of the member in which manually engageable finger guides 7 are disposed. The horizontal grooves 5 which are preferably disposed 180 degrees from each other across the circumference of the tubular member are merged by means of a pair of vertical guide grooves 6 which span the perimeter of the instrument and join to form a top guide groove 26 (illustrated in FIG. 10.) It is through these grooves that the manually engageable finger guides 7 are used to manipulate peripheral wires 11 within the device by means of radial arms 25 (illustrated in FIG. 8). FIG. 1 also depicts a catch basket 33 comprising peripheral wires 11, a main central wire 9 and two paracentral wires 10 which are joined at their distal tips 28. The catch basket also comprises a flexible netting 19. In FIG. 1 the catch basket is depicted as advanced distally by motion of the manually engageable finger guides 7 along horizontal guide grooves 5 which thereby advance peripheral wires 11, retractable guide 13 (shown in FIG. 4), main central wire 9 and paracentral wires 10.

FIG. 2 depicts a side view of the surgical extractor of FIG. 1 but wherein manually engageable finger guides 7 have been advanced circumferentially along vertical guide grooves 6 closing the catch basket 33. FIG. 3 depicts the surgical extractor wherein the shaft 2 has been advanced distally by rotation and wherein auger 12 has advanced distally into the extended catch basket 33.

FIG. 4 depicts a cross-sectional view of an embodiment of the surgical extractor with a threaded drive shaft 2 and its handle (control knob) 1 at the proximal end 32 of the instrument 31. The threaded portion of the drive shaft 3 is continuous with the non-threaded portion 16 of the drive shaft and the auger 12 within the tubular member 4 of the instrument 31. The tubular member 4 of the instrument 31 may be made of any suitable material such as, for example, plastic or the like, and may be oval in cross section and tapered at its distal end 8 to aid in insertion. The tubular member 4 of the instrument may also connect to a suitable irrigation source by means known in the art. The retractable guide 13 has a threaded central bushing 14 which surrounds the threaded portion 3 of the drive shaft 2. The retractable guide 13 can be made of any suitable material such as, for example, stainless steel or plastic. A stop ring 15 is present on the proximal non-threaded portion 16 of the drive shaft 2. The stop ring 15, threaded shaft portion 3, non-threaded shaft portion 16 and auger 12 may be made of any suitable material such as, for example, stainless steel. An expandable wire basket 33 enmeshed in flexible netting 19 is located at the distal end of the instrument 8. There are five wires 9–11 which make up the expandable basket 33. These include one main central wire 9, two paracentral wires 10, which assist the functioning of the main wire but are not absolutely necessary for practice of the invention, and two peripheral wires 11. Wires 9 and 10 pass through a distal fixed partition 17 and are fastened to the inferior portion of the retractable guide 13. The wires 9 and 10 are fixed to the retractable guide by means known in the art (for example adhesive or welding). The two peripheral wires 11 follow a similar course to the retractable guide 13 except they pass though the retractable guide 13 and possess capped or enlarged ends 18 on the proximal side of the retractable guide 13 restricting their movement in the distal direction. The flexible netting 19 of the basket 33 is made from a suitable flexible mesh made from suitable material, such as nylon, macron or the like. The wires 9, 10 and 11 are connected at the distal tip 28 of the catch basket 33 by welding, adhesive, hinging or other pivotally connected means known in the art. The surgeon grasps the instrument at the proximal end 32 by use of the finger handles 35 and places the thumb of the same hand on the control knob 1. The control knob 1 is then pushed into the instrument as one pushes a plunger into a syringe causing the drive shaft 2 and retractable guide 13 to move distally. The auger 12 and the expandable catch basket 33 also advance distally through the distal opening in the tubular member the same distance due to their connections with the drive shaft 2 and retractable guide 13, respectively.

FIG. 5 is the same elevated cross sectional view depicted in FIG. 4 except the drive shaft 2 has been advanced causing the catch basket 33 to extend from the distal end 8 of the instrument and assume its expanded configuration. The surgical instrument is also depicted in this same configuration in FIG. 1 except from a side view and not in cross section. FIGS. 4 and 5 also show the connection between the manually engageable finger guides 7 and the peripheral wires 11 of the basket within the tubular member 4 of the instrument. As the drive shaft 2 is advanced distally, the manually engageable finger guides 7 for the peripheral wires 11 are advanced the same distance due to their connection to the peripheral wires 11. FIG. 8, a cross sectional view along line 8 (FIG. 1), depicts the manually engageable finger guide 7 attachment to the peripheral wires 11 by the radial arm 25 of the manually engageable finger guides 7. The finger guide 7 movement is directed by the horizontal guide groove 5 seen in FIG. 1. Once the catch basket 32 has been advanced to its expanded open configuration as depicted in FIGS. 1, 5, and 9, the manually engageable finger guides 7 can be used to manipulate the expansion of the peripheral wires 11 thereby controlling the diameter of the catch basket 32. The manipulation of the peripheral wires 11 is afforded by movement of the manually engageable finger guide 7 in the horizontal guide groove 5 and in the vertical guide groove 6. The vertical guide groove 6 is wide enough to allow for adjustments in the manually engageable finger guides 7. Once the desired size of the catch basket 32 is maintained, the manually engageable finger guides 7 can be moved into the vertical guide grooves 6 pulling the peripheral wires 11 superiorly forming a closed catch basket 33 as shown in FIG. 2, which depicts the catch basket 33 in the extended closed configuration and shows the manually engageable finger guides 7 moved up to the top of the instrument by guidance in the vertical guide groove 6. FIGS. 2, 3, 10, 11 and 12 all display the manually engageable finger guides 7 together at the top of the instrument 31 in the vertical guide grooves 6 resulting in a closed catch basket 33.

FIG. 6 is an elevated cross sectional view of the instrument 31 with the catch basket 33 in the extended closed configuration. The peripheral wires 11 and finger guides are cut away in this view depicting their location at the top of the instrument when the catch basket 33 is in the closed configuration. FIGS. 3, 6, 10 and 11 depict the auger 12 advancing into the center of the closed catch basket 33. Advancement of the auger 12 is accomplished by rotating the control knob 1 on the end of the drive shaft 2. Rotation of the threaded portion 3 of the drive shaft 2 results in two opposing forces at the point of the threaded bushing 14 forcing the retractable guide 13 to move in the proximal direction (retract) and the drive shaft 2 and auger 12 to move in the distal direction (advance). If a firm object such as a cataract nucleus 21 has been encaptured within the catch basket 33, it will restrict the retraction of the retractable guide 13. As a result, the primary action of rotating the control knob 1 and drive shaft 2 will then be to advance the auger 12 into the nucleus 21. The auger 12 will advance until the stop ring 15 abuts against the distal fixed partition 17 stopping its advancement. Once the stop ring 15 is against the distal fixed partition 17, continued turning of the drive shaft 2, 16 can only cause retraction of the retractable guide 13 with the result that an object such as a cataract nucleus 21 encaptured within the catch basket will be forced against the auger 12.

FIG. 7 is an elevated cross sectional view of the instrument showing the closed catch basket 32 being retracted as a result of continued rotation of the drive shaft 2 after the stop ring 15 has contacted the distal fixed partition 17. The catch basket 33 has retracted as a result of the catch basket wires 10 and 11 direct attachment to the retractable guide 13 and the action of the retractable guide against the capped ends 18 of the peripheral wires 9.

FIG. 12, a side view, also depicts the catch basket 33 in the retracted closed configuration with the manually engageable finger guides 7 retracting along the top of the instrument in the top guide groove 26. The top guide groove 26 is best seen in the elevated view of FIG. 10. In this fashion, a nucleus 21 captured by the catch basket 33 will be concurrently crushed by the retracting catch basket 32 and ground up by the rotating auger 12, the pieces of the nucleus passing through the cavity 29 within the tubular member 4 of the instrument.

In a typical surgical procedure, using the instrument 31, a small appropriate incision, such as, for example, a sclera tunnel incision 30, preferably having a length of between 3 to 5 millimeters, may be made in the eye 22 as illustrated in FIG. 9, 10, 11 and 12. After the aforementioned incision is made, an anterior capsulotomy is performed using appropriate instruments, such as, for example, a cystotome or forceps. The aforementioned capsulotomy could be performed with the anterior chamber 27 maintained with viscoelastic or other suitable means common in surgical practice. Once the capsulotomy is completed, the cataractous nucleus 21 is prolapsed from the capsular bag using any of a variety of well known surgical maneuvers such as, for example, by utilizing a hydrodissecting cannula or cystotome. The nucleus 21 may be prolapsed into the anterior chamber 27 or positioned so that one pole of the nucleus 21 is above the plane of the anterior capsule 24.

Once the nucleus 21 has been prolapsed, the distal end 8 of the instrument 31 is inserted into the surgical incision 30 and advanced such that the distal end of the instrument 31 approaches the prolapsed pole of the nucleus in the anterior chamber 27. Once the instrument 31 is inserted into the anterior chamber 27, the surgeon may advance the catch basket 33 by grasping the finger handles 43 with his or her fingers and using the thumb of the same hand to push the control knob 1 into the instrument 31 much as a plunger in a syringe is advanced. The surgeon can then direct the nucleus 21 onto the open catch basket 33 with the use of a second instrument 20 inserted through a small stab incision in the cornea 34 as in FIG. 9. With the nucleus 21 now stabilized, the surgeon can use his or her thumb and index finger to manipulate the manually engageable finger guides 7 to expand and contract the peripheral wires 11 thereby adjusting the diameter of the basket 33. Once the appropriate diameter of the basket 33 is found, the thumb and index finger pull the manually engageable finger guides 7 superiorly in the vertical guide grooves 6 until the manually engageable finger guides 7 are together at the top of the instrument 31 closing the catch basket 33 around the nucleus 21. After the nucleus 21 has been completely enclosed within the catch basket 33, the second instrument 20 is removed from the eye 22 and the tubular member 4 of the instrument is held by one hand while the other hand begins rotating the control knob 1 at the proximal end of the instrument 31. Rotating the control knob 1 with a cataractous nucleus 21 captured in the catch basket 33 results in the advancement of the auger 12 into the captured nucleus 21 as in FIGS. 10 and 11. FIG. 10 depicts an elevated view of the instrument 31 with the auger 12 advanced into a nucleus 21 within the closed catch basket 33. The nucleus 21 is depicted in a cutaway fashion to best show the advanced auger 12. Continued rotation of the control knob 1 results in the nucleus 21 being simultaneously crushed by the retracting catch basket 33 and ground up by the rotating auger 12. The flexible netting 19 enclosing the nucleus 21 contains all but the smallest fragments of nucleus, resulting in virtually 100% of the nucleus mass being directed into the instrument cavity 29 of the instrument 31 by the auger 12. FIG. 12 is a side view of the instrument 31 with the nucleus 21 virtually completely removed from the anterior chamber 27 and the catch basket 33 almost completely retracted (this configuration is also depicted in the elevated cross sectional FIG. 7). Once the catch basket 33 has been retracted sufficiently, the instrument is removed from the eye. The remaining cortical material 23 is aspirated from the capsular bag 24 with any of a variety of well known aspiration devices. The surgery is then completed by inserting an intraocular lens, inflating the anterior chamber with fluid and testing the incision for water tightness with or without sutures. The anterior chamber can be maintained during the procedure with any of a variety of well known devices used for this purpose, or irrigation fluid could be passed through the instrument itself.

From the foregoing it will be seen that the invention provides a surgical instrument which is simple to operate and maintain and is particularly useful for safe, controlled, uncomplicated, removal of the nucleus from the eye.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A surgical instrument for removing a lens nucleus from an eye comprising:
   a tubular member having an opening at its distal end;
   a shaft at least partially disposed within the tubular member, the shaft having an auger disposed at its distal end and including a threaded portion;
   a retractable guide slidably disposed within the tubular member and threadably engaging the threaded portion of the shaft; and,
   a catch basket having an open position and a closed position, the catch basket operatively engaging the retractable guide such that, when the retractable guide is moved distally, the basket advances through the opening of the tubular member, and, such that, rotation of the shaft with respect to the retractable guide rotates the auger and retracts the basket at least partially into the tubular member.

2. A surgical instrument as defined in claim 1 further comprising means for moving the catch basket from the open position to a closed position.

3. A surgical instrument as defined in claim 2 wherein the moving means comprises a peripheral wire secured to a manually engageable finger guide.

4. A surgical instrument as defined in claim 3 wherein the manually engageable finger guide cooperates with a groove defined in the tubular member.

5. A surgical instrument as defined in claim 1 wherein the catch basket is secured to the retractable guide by at least one central wire and further comprising at least one peripheral wire coupling the basket to a manually engageable finger guide.

6. A surgical instrument as defined in claim 5 wherein the at least one peripheral wire slidably engages the retractable guide and wherein movement of the manually engageable finger guide moves the basket between the closed and open positions.

7. A surgical instrument as defined in claim 5 wherein a distal portion of the at least one central wire and a distal portion of the at least one peripheral wire form a portion the basket.

8. A surgical instrument as defined in claim 7 wherein the distal portions of the at least one central wire and the at least one peripheral wire are enmeshed in flexible netting.

9. A surgical instrument as defined in claim 1 further comprising a stop limiting distal movement of the shaft to a predefined travel length.

10. A surgical instrument as defined in claim 9 wherein the stop comprises a partition secured within the tubular member and a stop ring disposed on the shaft.

11. A surgical instrument as defined in claim 9 wherein rotation of the shaft only retracts the basket into the tubular member after distal movement of the shaft has been arrested by the stop.

12. A surgical instrument as defined in claim 9 wherein, after the stop prevents further distal movement of the shaft, continued rotation of the shaft causes the retractable guide to move proximally along the shaft to thereby retract the basket into the tubular member.

13. A surgical instrument as defined in claim 1 further comprising a handle on the proximal end of the shaft to facilitate rotation thereof.

14. A surgical instrument as defined in claim 1 further comprising finger handles located on the tubular member to facilitate sliding advancement of the shaft with respect to the tubular member.

15. A surgical instrument as defined in claim 1 wherein the tubular member has an oval cross section.

16. A method of removing a lens nucleus from an eye comprising the steps of:

inserting the instrument of claim 1 into the eye to be treated; directing the nucleus into said catch basket; enclosing the nucleus in said catch basket and retracting the catch basket into said instrument while grinding the nucleus with said auger; and removing said instrument from the eye.

* * * * *

UNITED STATES PATENT AND TRADEMARK OFFICE
CERTIFICATE OF CORRECTION

PATENT NO.   : 5,891,153
DATED        : April 6, 1999
INVENTOR(S)  : Randy Peterson It is certified that error appears in the above-identified patent and that said Letters Patent is hereby corrected as shown below:

On the title page, item [54] and Column 1:

In the title, "Extracted" should be --Extractor--.

Column 10, line 39, after "portion" (second occurrence), insert --of--.

Column 10, line 52, delete --only--.

Signed and Sealed this

Twentieth Day of June, 2000

Attest:

Q. TODD DICKINSON

*Attesting Officer*         *Director of Patents and Trademarks*